United States Patent [19]
Hatfalvi

[11] Patent Number: 5,628,734
[45] Date of Patent: May 13, 1997

[54] SPINAL NEEDLE WITH CURVED DISTAL END AND METHOD OF USING SAID NEEDLE IN A SPINAL INJECTION TO PREVENT POST DURAL PUNCTURE HEADACHE

[76] Inventor: Bela I. Hatfalvi, 15 Middlesex Dr., St. Louis, Mo. 63144

[21] Appl. No.: 409,503

[22] Filed: Mar. 23, 1995

[51] Int. Cl.⁶ .................................................. A61M 5/32
[52] U.S. Cl. .................................... 604/272; 604/158
[58] Field of Search .................................. 604/272–274, 604/158

[56] References Cited

U.S. PATENT DOCUMENTS

| | | | |
|---|---|---|---|
| 3,097,647 | 7/1963 | Roehr | 604/272 |
| 4,684,369 | 8/1987 | Wildemeersch | 604/272 |
| 4,759,746 | 7/1988 | Straus | 604/51 |
| 4,958,901 | 9/1990 | Coombs | 604/44 |
| 5,284,476 | 2/1994 | Koch | 604/274 |
| 5,480,389 | 1/1996 | McWha et al. | 604/165 |

FOREIGN PATENT DOCUMENTS

| | | | |
|---|---|---|---|
| 1536352 | 8/1968 | France | 604/158 |
| 1168224 | 7/1985 | U.S.S.R. | 604/272 |

OTHER PUBLICATIONS

Illustrated Handbook in Local Anaesthesia, Year Book Medical Publishers, Inc., 1969, pp. 112–129.
Headache Journal, vol. 17, May 1977, pp. 64–66.

*Primary Examiner*—Corrine M. McDermott
*Attorney, Agent, or Firm*—Howell & Haferkamp, L.C.

[57] ABSTRACT

Various embodiments of spinal needles, each having a curvature, are used in a method of administering a spinal anesthetic while preventing the development of post dural puncture headache.

6 Claims, 3 Drawing Sheets

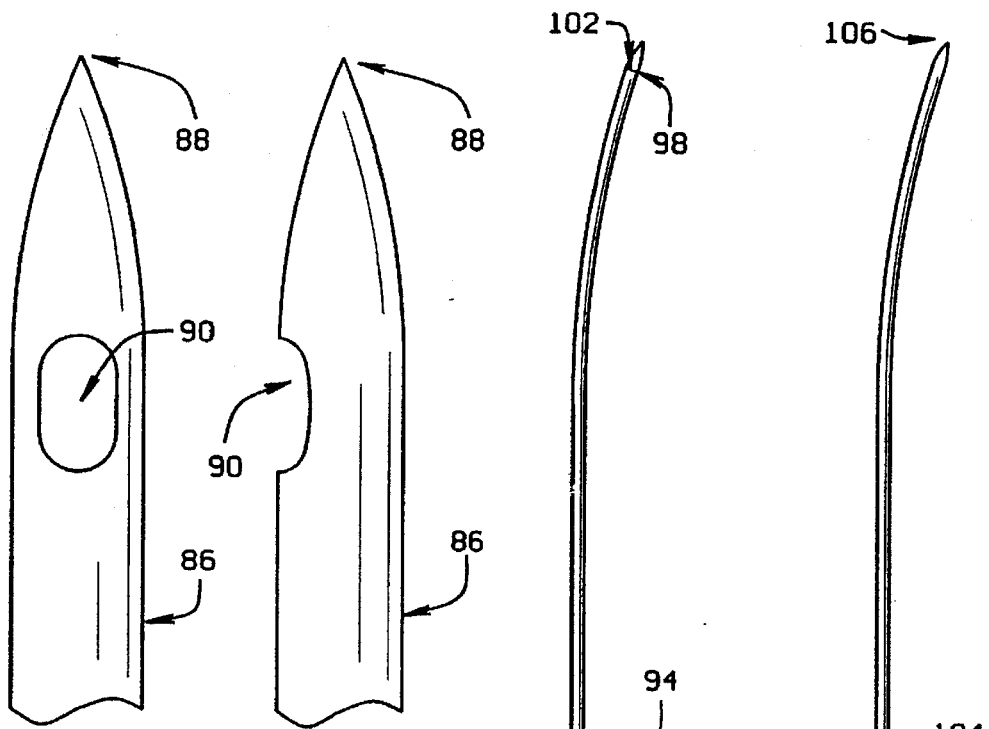
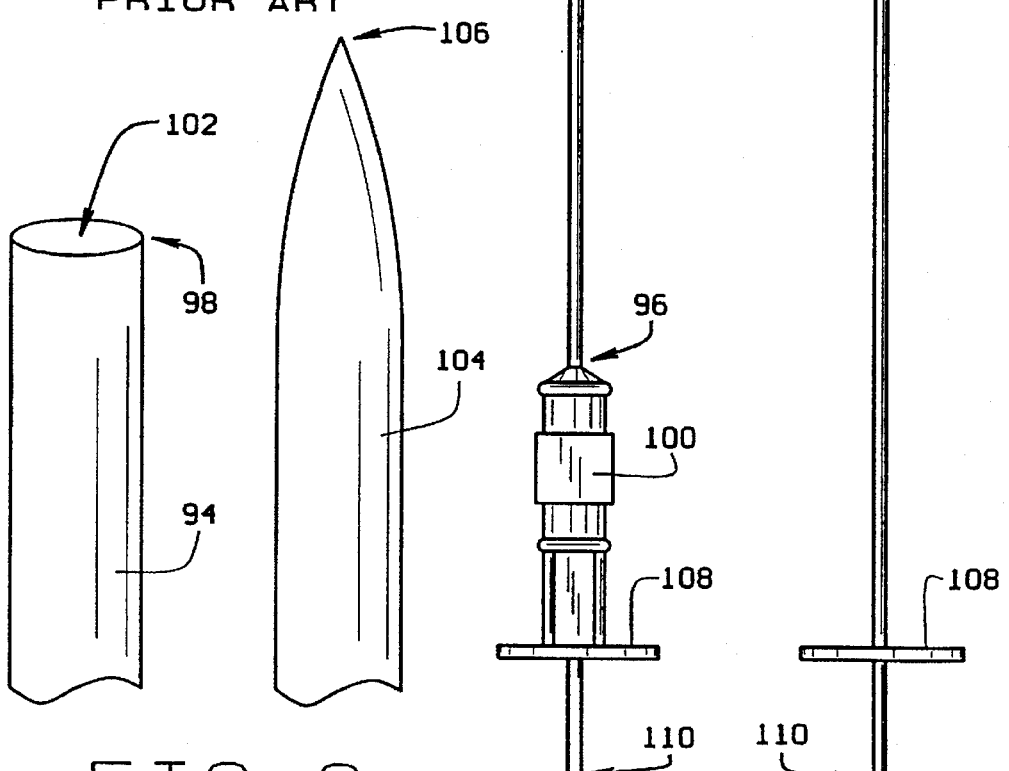
FIG. 6 PRIOR ART
FIG. 8
FIG. 7A  FIG. 7B

SPINAL NEEDLE WITH CURVED DISTAL END AND METHOD OF USING SAID NEEDLE IN A SPINAL INJECTION TO PREVENT POST DURAL PUNCTURE HEADACHE

BACKGROUND OF THE INVENTION (1) Field of the Invention

The present invention pertains to a spinal needle having a slight curvature at its distal end and a method of using the spinal needle in administering a spinal anesthetic while preventing the development of post dural puncture headache.

(2) Description of the Related Art

Headache continues to be a common complication associated with subarachnoid puncture. The cause of headache pain is believed to be the loss of cerebrospinal fluid from the subarachnoid compartment of the spine, through the puncture site into the epidural compartment of the spine, with a resulting caudal movement of the cranio-spinal contents when the patient subsequently assumes an upright position.

The majority of physicians prefer the use of the midline approach for spinal puncture. Generally, with the midline approach, the spinal injection is made at the center of the patient's back with the needle oriented in a plane parallel to the centerline of the spine. The needle tip is inserted into the back in a straight line toward the midline of the spine between the second 10 and third 12 lumbar vertebrae, a direction generally represented by the arrow (A) shown in FIG. 3.

The applicant administered his first spinal anesthetic employing the midline approach. However, after unsuccessful attempts, a lateral approach, a technique used in difficult situations, was used and was successful on the first attempt. The lateral approach technique was so easy to perform that the applicant has exclusively used this technique with a 20 gauge Becton Dickinson® (B-D) Quincke point needle. In over twenty years of practice over four thousand spinal anesthetics were performed by the applicant and by resident interns under his close supervision utilizing the lateral approach. The lateral approach differs from the midline approach by the needle being introduced at a point spaced two to three centimeters laterally from the midline of the spine. Due to the lateral positioning, the needle must pass through more muscle tissue before reaching the spine than in the midline approach. All of the over four thousand spinal anesthetics were without headache. The absence of post dural puncture headache led the applicant to study the difference between lateral and midline puncture of the dura mater. This led to the idea that the angle at which the needle pierces the dura and arachnoid membranes, rather than the size of the needle, was the most important factor in the occurrence of post dural puncture headache. The applicant has conducted several different tests in investigating this hypothesis. In the investigations, studies were conducted on two anatomical models—a human dura model and a lumbar spine model—and on an artificial dura model.

In the studies conducted on the human dura model, pieces of lumbar dura with its attached membranes were removed from human cadavers and sealed over a small opening in a section of one inch plastic tubing. The tubing was closed at one end and was connected to a water manometer inserted at its opposite end. The tubing was filled with water tinted with a blue dye. A syringe, filled with the blue tinted water, was attached to the tubing to allow the introduction or removal of water from the tube to vary the water pressure in the manometer. The entire tube and surrounding lumbar dura were emersed in a saline-filled vessel. Pressure in the manometer was set at 200 millimeters and the dura model was ready for several spinal needle puncture tests.

Perpendicular punctures, punctures made at the midline, resulted in a continuous leakage of fluid from the punctures as long as positive pressure existed in the system manometer. After pressure in the manometer was reduced to zero due to the leakage, further repressurization of the "dural space" by injecting additional tinted fluid into the manometer from the syringe caused more leakage to occur.

Resetting the system with 200 millimeters of tinted fluid in the manometer, puncturing the dura at a 35 degree lateral angle from the midline with the bevel of the needle tip facing the dura resulted in total fluid pressure loss in the manometer due to leakage just as in the perpendicular puncture experiments. However, as soon as pressure was reapplied to the system by the syringe, the leakage from the punctures ceased immediately and permanently. Despite any pressure change thereafter, from 0 to 570 millimeters of tinted fluid in the manometer, leakage did not reappear. It was also observed that puncture of the dura at an angle caused the colored fluid to leak in a stream from the puncture at the same angle as the puncture.

The perpendicular puncture and angled puncture experiments were performed on 36 dura specimens with 20, 22 and 25 gauge B-D sharp beveled needles, with a total of 324 punctures.

In the angled puncture experiments, measurements were made of the minimum needle angle to the spine midline necessary to obtain a prompt closure of the valvular opening formed in the dura by the needle tip puncture. These measurements were made with gradually decreasing angles (i.e., gradually approaching perpendicular needle orientation) of the piercing needle in 5 degree increments from 45 degrees. When the needle orientation reached 15, 10 and 5 degrees from the perpendicular with needles of 20, 22 and 25 gauge, constant leakage occurred with positive pressure in the manometer. The leakage still occurred after the initial manometer pressure was allowed to decrease to zero and the manometer was then repressurized by adding additional fluid to the manometer from the syringe. A needle angle of 35 degrees resulted in closure of the valvular flap formed by the punctured opening in all cases.

The results of these tests led to the investigation of the importance of the position of the beveled opening at the needle's tip relative to the dura. Several of the test punctures revealed that perpendicular punctures will leak, regardless of the bevel's rotation and size of the needle.

In conducting the lumbar tissue model experiments, the second and third lumbar vertebrae with the overlying skin, subcutaneous tissue, muscles, interspinous ligaments and dura intact were removed from a cadaver. Needles of various sizes were inserted perpendicularly to the surface at the midline into the subarachnoid space. An x-ray examination in a cranio-caudal direction (in a direction from the head down the length of the spine) was then carried out to determine the exact position of the needles as affected by the direction of the bevel tip. The X-rays indicated that the needle bevel orientation strongly influenced the path traversed by a flexible needle in spinal injections. The X-rays showed that a 20 gauge needle, perpendicularly introduced at the midline, remained in the median plane and entered the subarachnoid space also in the midline. However, thinner gauged needles (22 and 25 gauge) perpendicularly introduced at the midline entered the subarachnoid space in a tangential manner. As the needle was introduced through the tissue toward the subarachnoid space of the spine, the density of the tissue caused the needle's path to bend or curve in a direction opposite to the side faced by the bevel. A 22 gauge needle introduced at the midline with its bevel facing to the left curved to the right as it passed through the tissue. A 25 gauge needle introduced at the midline and with its course guided by a 21 gauge introducer also curved in a direction opposite to the side faced by the bevel.

In the experiments conducted on the artificial dura model, a one-inch thick "dura" was constructed from an elastic dental impression powder. This model was used to illustrate the characteristics of the three primary modes of needle bevel penetration through the dura. A schematic representation of the dura model 14 used is shown in FIG. 5. This model shows the characteristics of dural punctures with sharp beveled needles, emphasizing the differences in the valvular flap openings cut through the dural mater by the needle opening beveled edge from the primary modes of perpendicular and tangential puncture of the dura.

At the left side in FIG. 5, a perpendicular puncture of the dura 14 results in a swinging-door-like valvular flap 16 formed in the dura by the bevel opening edge 18 of the needle 20. The valvular flap 16 of this type can remain open by the pressure of the cerebrospinal fluid, which is constantly present in the subarachnoid space 22 and can be reproduced by the physical activity of the patient, and by negative epidural relative pressure in the epidural space 24. With the valvular flap 16 formed by the perpendicular puncture being capable of swinging to either the subarachnoid side 22 of the puncture or the epidural side 24 of the puncture, the probability of cerebrospinal fluid leakage is high and the probability of resulting headache is high.

The puncture shown at the center of the dura model 14 in FIG. 5 is made with the needle 20' oriented at an angle relative to the dura 14 with the bevel opening 18' of the needle facing away from the dura and toward the operator making the injection. The valvular flap 16' formed by the needle in the dura mater is able to deflect into the epidural space 24. With this type of puncture opening, cerebrospinal fluid leakage may be maintained by both subarachnoid positive pressure of the fluid and epidural negative pressures. With this particular type of puncture, pressure from outside the valvular flap in the epidural space 24, in the form of an epidural saline or blood patch, may help to seal off the opening as the subarachnoid and epidural spaces reach equilibrium pressure.

The right side of FIG. 5 illustrates the dura puncture mode which results in the least leakage or no leakage of cerebrospinal fluid through the puncture opening. The valvular flap 16" formed by the puncture is made by the bevel opening 18" of the needle 20" facing the dura 14. This flap 16" will be able to close itself by means of increased cerebrospinal fluid pressure in the subarachnoid space 22 from restitution of the fluid and/or early ambulation, cough, stretching, or some other physical activity of the patient.

The above studies suggested to the applicant that a tangential puncture, with the needle bevel opening facing the dura, is the most critical factor in avoiding post dural puncture headache. The importance of the bevel position is most appreciated after the needle is withdrawn from the dura and the healing process begins to take place. At first there will be an uncontrollable cerebrospinal fluid escape through the puncture, until pressure equilibrium is established between the subarachnoid and epidural spaces. Fluid will flow from a high pressure area as long as positive pressure exists and an escape route is open. The flow of cerebrospinal fluid after every dural puncture is a definite impediment to wound healing. However, after a momentary equilibrium in fluid pressure is reached between the subarachnoid and epidural spaces, the valvular flap formed by the puncture of the type shown at the right in FIG. 5 will close from the increasing pressure of cerebrospinal fluid restitution resulting from the patient's physical activity, and the valvular flap will not reopen, thus preventing headache. The role of cerebrospinal fluid in terms of its replacement capacity is important (500 ml per 24 hours, or more) in providing the closing force on the valvular opening 16" of the tangential dural puncture. The closing force on the valvular opening is directly proportional to the area of the valvular flap (force= pressure×area). Enlarging the valvular opening by using a large needle will increase the cerebrospinal fluid pressure on the valve surface and close the valve forcefully. The larger needle will also deviate less and allow greater control and more accurate placement of the puncture.

Since the density and depth of the material through which the beveled needle travels determines the degree of bending, even midline punctures can and will enter the dura somewhat as though they were done with a lateral approach with the bevel facing the dura. However, since finer bevel needles cannot be controlled as well as large needles in terms of dura entry point (or even dura entry itself), it seemed to the applicant reasonable to reexamine the use of larger beveled needles with the lateral approach.

From the applicant's investigations, it was determined that it was desirable to use a larger needle (20 gauge needle) in spinal injections because the larger needle would deviate less and allow greater control and a more accurate placement of the puncture. Also, the larger needle creates a larger valvular flap opening as it punctures the dura. The larger valvular flap will increase the pressure of cerebrospinal fluid on the valve surface and close the valve forcefully once the needle is withdrawn and the presence of cerebrospinal fluid reaches an equilibrium across the puncture opening. The midline approach is also preferable over the lateral approach. However, using a larger needle with the midline approach may result in the deflection of the needle being insufficient to penetrate the dura at the optimal angle of at least 35 degrees.

It is, therefore, an object of the present invention to provide an improved spinal injection needle, preferably used in the midline approach, where the needle is specifically designed to penetrate the dura with its bevel opening facing the dura and with the incident angle of the needle being at least the optimal angle of 35 degrees. It is also an object of the invention to provide an improved spinal injection needle where the needle is specifically designed to penetrate the yellow ligament of the spine and the needle tip enter the epidural space without penetrating the dura. It is also an object of the present invention to provide methods of using the needles of the invention in spinal injections avoiding the development of post dural puncture headache.

SUMMARY OF THE INVENTION

The spinal injection needle of the present invention has a construction that is similar to conventional needles such as the Quincke and Touhy needles. The needle has a cannula with opposite proximal and distal ends. A hub is provided at the proximal end of the needle for connecting the needle to a syringe or other equivalent type of medicament dispensing apparatus. The distal end of the needle has a beveled opening at the tip of the needle.

The improvement of the needle of the invention over the prior art is in a slight bend or curve formed in the needle. The curvature gives the cannula opposite concave and convex exterior surfaces. In the embodiment of the needle used to penetrate the dura, the beveled opening at the cannula distal end faces in a direction away from the concave surface and toward the convex surface. In the embodiment of the needle used to penetrate only the epidural space, the beveled opening faces away from the convex surface and toward the concave surface.

The method of using the needle in administering a spinal anesthetic preferably uses the midline approach. First, a stylet is inserted into the needle from the needle proximal end. The stylet has a beveled surface at its distal tip that lies adjacent the plane of the needle opening beveled edge. The stylet prevents tissue from entering the needle as the needle is introduced through tissue. The second and third lumbar vertebrae are located in the back and the needle distal end is positioned at a point on the midline of the individual's spine at the spacing between the second and third lumbar vertebrae. The curvature of the needle is positioned in a plane parallel to the midline with the needle curvature pointing the distal tip upwardly. The needle is introduced into the back in the direction of a straight line toward the center of the spacing between the second and third vertebrae. The curved portion of the cannula causes the cannula distal end to deviate upwardly from the straight line and tangentially penetrate the spine.

In the embodiment of the needle designed for dura mater penetration, due to the relative positioning of the bevel opening and the needle curvature, the needle distal end penetrates the dura with the bevel opening facing the dura. In this manner, the penetration of the bevel opening forms a valvular flap that extends from the dura into the subarachnoid space.

The stylet is then removed and the injection is then made through the cannula into the dura and the needle withdrawn in a conventional manner. The leakage of cerebrospinal fluid from the subarachnoid space through the puncture to the epidural space is permitted until an equilibrium pressure across the puncture is achieved. At this point, with the removal of the cerebrospinal fluid pressure from the valvular flap formed at the puncture opening, the flap closes over the puncture. The reproduction of cerebro-spinal fluid is then induced by physical activity of the patient. The restitution of cerebro-spinal fluid increases the fluid pressure on the valve surface and holds the valve closed, healing the puncture of the dura and avoiding post dural puncture headache.

In the embodiment of the needle designed for penetration only into the epidural layer or space of the spine, a stylet is first inserted through the needle so that a beveled tip of the stylet is positioned substantially in the same plane as the needle bevel opening. Due to the relative positioning of the bevel opening and the needle curvature, the needle distal end penetrates the spine yellow ligament (the ligamentum flavum) and enters the epidural space with the bevel opening facing into the epidural space and away from the dura. The curvature of the needle, in particularly at its distal end, enables the entire bevel opening at the needle tip to be positioned in the epidural space while preventing the tips of the stylet and of the epidural needle from contacting and potentially penetrating the dura of the spine.

The stylet is removed and the epidural catheter introduced for the injection of desired anesthetic solution injection into the epidural space is then made through the cannula and the needle is withdrawn in a conventional manner. Because of the specific design of the epidural needle, dura penetration and a resulting headache is avoided.

BRIEF DESCRIPTION OF THE DRAWINGS

Further objects and features of the present invention are revealed in the following detailed description of the preferred embodiments of the invention and in the drawing figures wherein:

FIG. 6 shows distal tips of a prior art Sprottle type needle;

FIGS. 7A and 7B show a further embodiment of the spinal injection needle of the invention; and FIG. 8 shows the distal ends of the cannula and stylet of the needle of FIG. 7.

DESCRIPTION OF THE PREFERRED EMBODIMENTS

The present invention concerns improvements to spinal injection needles. The first described embodiment of the invention is preferably used in penetrating the subarachnoid space of the spine through the dura. The later described embodiments are preferably used in penetrating only into the epidural space of the spine. All of the embodiments are designed to avoid the occurrence of post dural puncture headache.

Figures 1, 2, 3:
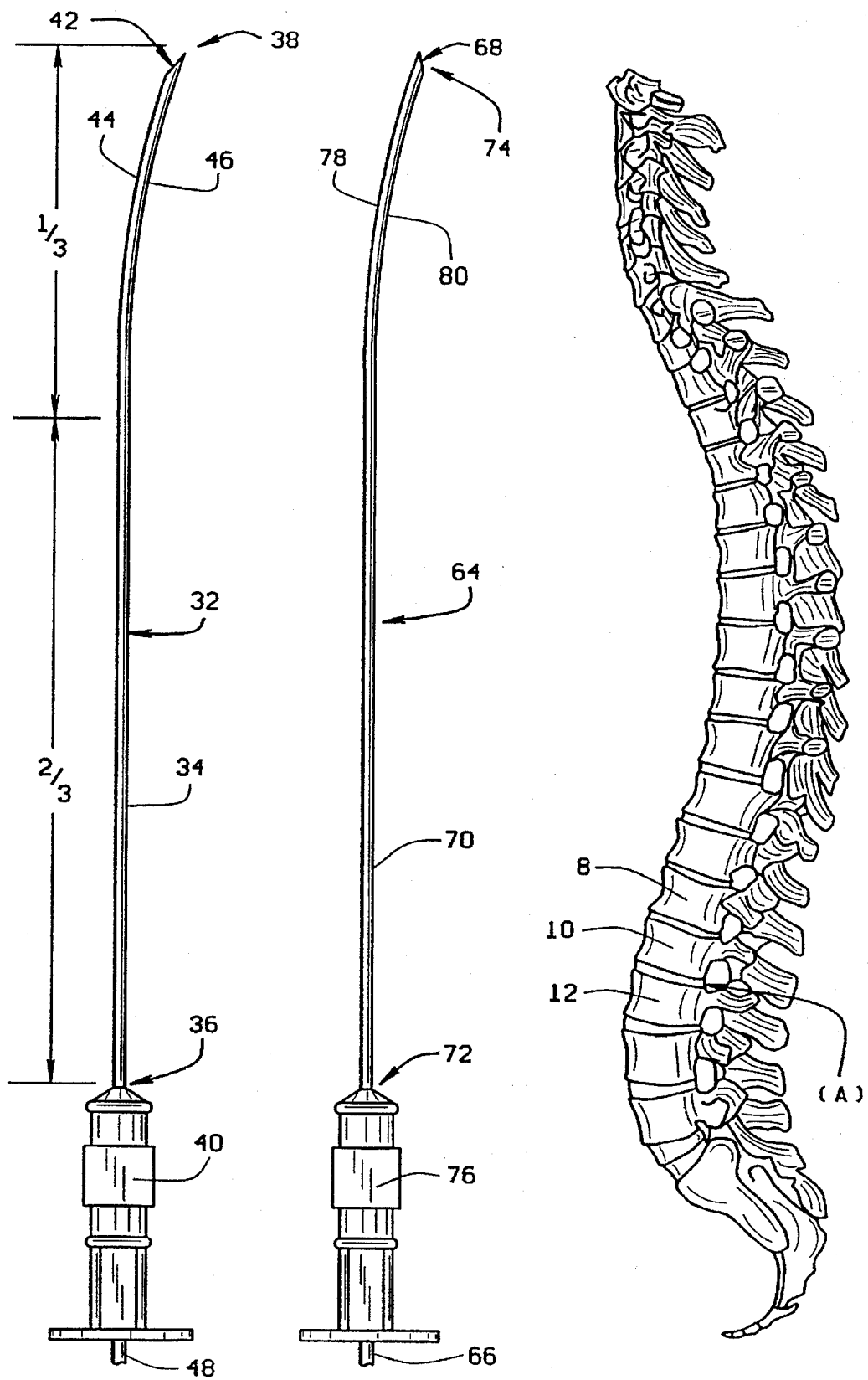
FIG. 1 shows the spinal injection needle of the invention which is designed for dura mater penetration.
FIG. 2 shows the spinal injection needle of the invention designed for penetration only into the epidural space of the spine.
FIG. 3 shows a representation of the left side of the human spine.

The spinal injection needle 32 of the present invention designed to penetrate the dura mater of the spine is shown in FIG. 1. The materials employed in constructing the needle 32 of the invention are the same as those employed in constructing conventional needles. The needle of the invention is comprised of a cannula 34 having an elongated configuration with opposite proximal 36 and distal 38 ends. A hub 40 is secured to the cannula proximal end 36. The hub 40 is the same as that employed on conventional spinal needles and may be employed to connect the needle to a syringe or some other type of medicament dispensing apparatus. A beveled opening is provided at the cannula distal end 38. The bevel opening serves as an exit opening for the cannula tubular interior. A beveled edge 42 of the needle distal end surrounds the opening. In the preferred embodiment, the cannula 34 is 20 gauge. However, the inventive design of the needle may be employed in any size or type of spinal injection needle as will be illustrated herein.

The improvement made in the spinal injection needle 32 of the invention over the prior art needles is in the slight bend or curvature formed in the needle cannula. As shown in FIG. 1, the curvature is located adjacent its distal end 38. In the embodiment of the invention shown, the needle cannula 34 will extend from its proximal end 36 in a straight line for approximately two-thirds of its total longitudinal length between its proximal end 36 and distal end 38. The curvature in the cannula is formed in the remaining one-third of the cannula length adjacent the distal end 38. As the cannula extends through this one-third of its length, it curves or bends laterally to one side away from the side of the cannula from which the bevel opening 42 faces. This gives the one-third length of the cannula a convex surface 44 adjacent the bevel edge opening 42 and a concave surface 46 opposite the convex surface and the bevel opening. The lateral extent of the curvature shown in FIG. 1 preferably ranges between three percent (3%) and five percent (5%) of the overall longitudinal length of the cannula 34. However, the lateral deflection can vary fractions of a percentage from the preferred range of lateral deflection without significantly affecting the functioning of the needle of the invention due to variance in the densities of patient body tissues through which the needle is introduced. Furthermore, in variant embodiments of the needle the curvature can be gradual along the entire length of the cannula from its proximal to is distal end. The curvature can also increase from the cannula proximal end to its distal end, with the curvature being more pronounced as it approaches the needle distal end.

The curvature formed in the distal one-third of the needle's overall longitudinal length does not obstruct or hinder the passage of fluid through the center of the cannula 34. The cross-sectional area of the cannula interior bore (not shown) remains substantially constant throughout the entire length of the cannula. A center line extending through the cannula bore will extend in a straight line for the two-thirds of the cannula length adjacent its proximal end 36 and will then extend in a curved line for the remaining one-third of the cannula length adjacent its distal end 38.

A stylet 48, only the proximal end of which can be seen in FIG. 1, is inserted through the center of the needle cannula. The stylet has a curvature that matches that of the needle. The stylet also has a beveled plane at its distal tip that matches the beveled edge of the needle tip opening and lies in the same plane as the edge of the needle tip opening. The stylet therefore has opposite concave and convex surfaces positioned relative to its beveled tip surface substantially identically to the relationship between the needle opening bevel edge and the needle surfaces. The style, inserted into the needle prevents any tissue from entering the needle through the beveled opening as the needle is introduced through the tissue.

The method of using the spinal injection needle 32 of the present invention in administering a spinal anesthetic preferably employs the midline approach. The midline approach is known to the ordinary skilled artisan and, therefore, will not be described here in detail. A description of this method can be found in the *Illustrated Handbook of Local Anaesthesia*, Year Book Medical Publishers, Inc., 1969. It should be understood, however, that the injection needle 32 of the invention may also be employed in a spinal injection made using the lateral approach.

Figures 4, 5:
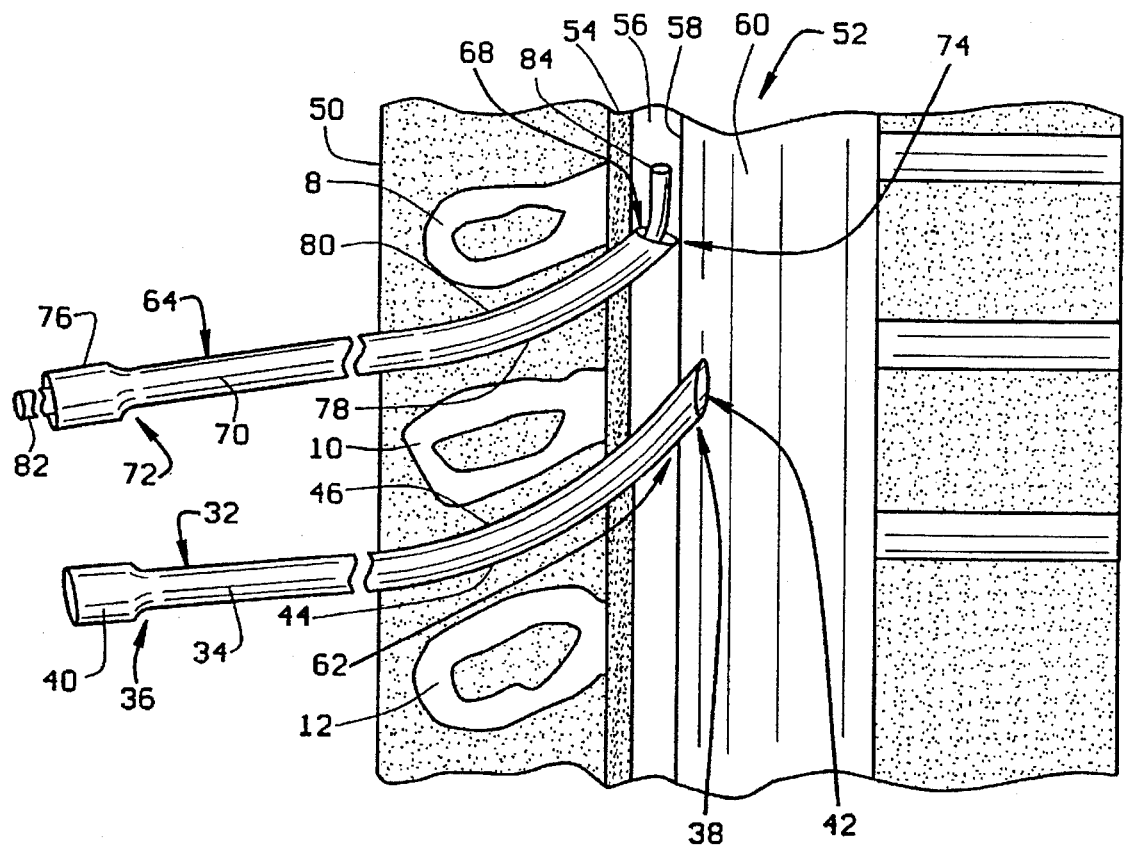
FIG. 4 is a partial schematic representation of the penetration into the epidural space of the epidural spinal needle of the invention and the penetration into the dura of the dural spinal needle of the invention.
FIG. 5 is a partial schematic representation of various different modes of dura mater penetration.

The second 10 and third 12 lumbar vertebrae are first located in the back. The needle distal end 38 is then positioned at a point on the midline of the individual's back at the spacing between the second and third lumbar vertebrae. The curvature adjacent the needle distal end, extending the tip of the needle upwardly, is positioned in a plane parallel with the midline and bisecting the center of the spine. The needle is next introduced into the back in the direction of a straight line toward the center of the spacing between the second and third vertebrae, substantially in the direction represented by the arrow (A) shown in FIG. 3. The curved portion of the cannula 34 causes the cannula distal end 38 to deviate upwardly from the straight line of introduction as the needle is introduced through the body tissue 50 toward the spine 52. The needle distal end 38 passes through the body tissue 50 and the layer of yellow ligament 54 surrounding the spine. The needle next passes through the epidural space 56 and penetrates the dura mater 58. As shown in FIG. 4, the cannula distal end 38 penetrates the dura mater 58 with the preferred orientation of the bevel opening edge 42 referred to earlier with regard to FIG. 5. The distal end 38 penetrates through the layer of dura with the bevel opening 42 facing the dura, thereby forming a valvular flap in the dura that extends into the subarachnoid space 60 of the spine. Following penetration of the dura, the stylet 48 is removed from the needle.

The injection is next made through the cannula 34 into the dura and the cannula is withdrawn in a conventional manner. The leakage of cerebrospinal fluid from the subarachnoid space 60 through the puncture 62 formed in the dura by the needle is permitted until an equilibrium pressure is achieved across the dura between the subarachnoid space 60 and the epidural space 56. At this point, with the fluid pressure gradient across the puncture 62 reduced to zero, the valvular flap formed in the dura, the valvular flap 16" being of the type shown on the right side of FIG. 5, closes over the puncture in the dura. The patient is then prompted to exert some physical activity either through stretching, coughing, etc. to initiate the reproduction and restitution of the cerebrospinal fluid in the subarachnoid space. The restitution of cerebrospinal fluid increases the fluid pressure on the surface of the closed valvular flap 16" and holds the valvular flap closed. This results in a healing of the puncture of the dura while avoiding post dural puncture headache.

In the preferred embodiment of the invention, the needle 32 is formed with a 20 gauge cannula. Employing a cannula of this size increases the size of the valvular flap 16" cut through the dura when the distal end of the cannula punctures the dura. The increased size of the valvular flap enhances the ability of the cerebrospinal fluid pressure to hold the valve flat in its closed position following restitution of the cerebrospinal fluid.

FIG. 2 shows a further embodiment of the spinal injection needle 64 of the present invention. This needle also has a stylet 66 inserted through the needle proximal end. The distal end of the stylet has a beveled surface that matches the opening bevel edge of the needle 64 just as in the previous embodiment. The stylet also has a curvature that matches that of the needle. The embodiment shown in FIG. 2 is designed to penetrate the yellow ligament of the spine to position the opening 68 at the distal end of the needle in the epidural space of the spine without puncturing the dura. The needle 64 is frequently employed in inserting a catheter into the epidural space of the spine to enable a continuous administration of an anesthetic or other medicament to the epidural space. Typically, the needle 64 is first introduced into the spine and the stylet 66 removed. Then the catheter tube is inserted through the interior bore of the needle until its distal end projects into the epidural space. The needle 64 is then removed from the spine leaving the catheter in place. Needles of this type typically are of a larger gauge than the spinal injection needles of the type shown in FIG. 1. The prior art epidural needles are substantially straight, large gauge needles. When introduced into the epidural space, great care must be taken to avoid unintentional puncture of the dura and the resulting headache.

The materials employed in constructing the needle 64 of the invention are the same as those employed in constructing conventional needles. The needle of the invention 64 is comprised of a cannula 70 having an elongated configuration with opposite proximal 72 and distal 74 ends. A hub 76 is secured to the cannula proximal end. The hub is a conventional hub employed on epidural injection needles.

The improvement made in the epidural injection needle 64 over prior art needles is in the slight bend or curvature formed in the needle cannula, preferably along its entire length. In the preferred embodiment of the invention, the cannula 70 will extend from its proximal end 72 in a continuous curve to its distal end. Because in use the epidural needle is not introduced into tissue as far as the dural needle, its curvature is more pronounced. The cannula curves or bends toward the side of the cannula from which the bevel opening 68 at the distal end faces. This gives the cannula a convex surface 78 facing away from the bevel edge opening 68 and a concave surface 80 opposite the convex surface and facing in the direction of the bevel opening 68. In other embodiments, the curvature of the epidural needle can be located more toward its distal end as in the first embodiment. The curvature can also increase exponentially from the cannula proximal end to is distal end, with the curvature being more pronounced as it approaches the needle distal end.

The method of using the epidural needle 66 in administering a spinal anesthetic preferably employs the midline approach; however, the needle may also be used in a lateral approach. As illustrated in FIG. 4, the first 8 and second 10 lumbar vertebrae are first located on the patient's back. The needle distal end 74 is then positioned at a point on the midline of the patient's back at the spacing between the first and second vertebrae. The needle curvature, extending the tip of the needle upwardly, is positioned in a plane parallel with the midline and bisecting the center of the spine. The needle is then introduced into the back in the direction of a straight line toward the center of the spacing between the first and second vertebrae, substantially in the direction represented by arrow (A) in FIG. 3. The curvature of the cannula 70 causes the cannula distal end 74 to deviate upwardly from the straight line of introduction as the needle is introduced through the body tissue 50 toward the spine 52. The needle distal end 74 passes through the body tissue 50 and the layer of yellow ligament 54 (the ligamentum flavum) surrounding the spine. This penetration can be sensed by the physician from the resistance of the yellow ligament to penetration. As shown in FIG. 4, the curvature of the needle causes the distal end 74 to enter the epidural space 56 at an angle with the needle distal end 74 curving away from the dura 58 and projecting the needle opening 68 through the epidural space 56. In this way, the curved configuration of the epidural needle 66 enables positioning of the needle distal end opening 68 in the epidural space while avoiding puncturing the dura mater 58. Following penetration, the stylet is then removed. The curved configuration of the needle also facilitates the insertion of a catheter 82 through the needle bore and into the epidural space without the catheter distal end 84 coming into contact with the dura 58 and actually being redirected through the epidural space 56 by the needle avoiding any probability of puncturing the dura with the catheter end. With the catheter in place, the needle 66 is then withdrawn over the catheter. In this manner, a catheter is positioned in the epidural space of the spine while avoiding puncturing of the dura and its resulting post dural puncture headache with the epidural needle 66 of the invention.

FIG. 6 shows the distal tip of a prior art spinal injection needle. The tip schematically shown in FIG. 6 is of a Sprotte-type needle. The distal end 86 of the needle comes to a tip 88 and an opening 90 passes through a side of the needle adjacent its tip. The opening 90 communicates with the interior bore of the needle cannula. The left side view of FIG. 6 is looking at the needle opening 90, and the right side view of FIG. 6 is looking at the same opening with the needle tip turned 90 degrees. In use of a needle of this type, introduction of the needle into the spine is made perpendicular to the midline. Because there is no bevel at the needle tip, the needle is introduced perpendicularly into the spine. Needles of this type are used in administering injections into the subarachnoid space of the spine and the epidural space of the spine. The prior art Whitacre needle has a similar construction to the Sprotte needle shown, except that its tip has a configuration of a pencil point rather than the curved tip of the Sprotte needle shown in FIG. 6.

In use of prior art needles of this type in administering spinal injections, the needle is introduced perpendicularly at the midline of the spine. The needle tip punctures the dura and enters the subarachnoid space when administering an anesthetic into the subarachnoid space, or only penetrates the yellow ligament of the spine and enters the epidural space when administering an anesthetic to the epidural space.

Prior art needles of this type are disadvantaged in that, because the side opening 90 removes material from the side of the needle cannula, the needle tip is prone to bend at times at the needle cross section containing the opening 90. Additionally, at times the entire side opening 30 of the needle will not penetrate into the desired space. For example, in making an injection into the subarachnoid space of the spine, it is possible that the distal end of the needle is not inserted a sufficient distance through the dura resulting in only a portion of the side opening 90 being positioned within the subarachnoid space behind the dura. The remaining portion of the opening 90 is outside the subarachnoid space in the epidural space. In administering an anesthetic, only a fraction of the anesthetic will be delivered to the subarachnoid space as intended. The remaining anesthetic will be delivered to the epidural space.

FIGS. 7 and 8 illustrate a further embodiment of the spinal injection needle of the present invention. This embodiment is designed to overcome the shortcomings of injection needles of the type shown in FIG. 6. The needle of FIGS. 7 and 8 is similar to previously described embodiments in that it is comprised of a cannula 94 having an elongated configuration with opposite proximal 96 and distal 98 ends. A hub 100 is provided on the proximal end of the needle and is the same as that employed on conventional spinal needles. An opening 102 is provided at the needle distal end 98. The opening 102, contrary to the previously described embodiments, is not a beveled opening. The opening 102 is positioned in a plane that is perpendicular to the center line of the needle cannula 94 at the needle distal end 98. A stylet 104 is inserted through the interior of the needle cannula 94. The stylet 104 has a length dimensioned so that the stylet distal end 106 projects out from the opening 102 of the cannula. The stylet distal end 106 is configured in a point in the same manner as the Sprotte needle or the Whitacre needle. A flange 108 is secured adjacent the needle proximal end 110. The flange 108 abuts against the cannula hub 100 with the stylet 104 inserted through the center of the cannula as shown in FIG. 7A. FIG. 8 shows a partial view of the distal ends of the cannula 94 and the stylet 104. As can be seen in this drawing figure, the stylet distal end 106 is configured to come to a point at its center line with no beveled edges.

As shown in FIGS. 7A and 7B, the cannula 94 and stylet 104 are provided with a slight bend or curvature. In the preferred embodiment, the curvature is formed adjacent the distal ends of the cannula and stylet. However, as in the previously described embodiments of the invention, the curvature can extend along the entire longitudinal length of the cannula and stylet and may increase exponentially as it approaches the distal ends of the cannula and stylet.

Use of the needle embodiment shown in FIGS. 7A and 7B are substantially identical to that of previously described embodiments of the invention. The stylet 104 is first inserted through the cannula 94 to their relative positions shown in FIG. 7A. The midline approach is preferably used in administering a spinal anesthetic using the needle of 7A. The injections are made into the subarachnoid space of the spine through the dura or into the epidural space of the spine through the yellow ligament in the same manner as previously described embodiments of the invention. The curvature of the cannula and stylet cause the needle distal end to enter the spine tangentially, just as in the previously described embodiments. Once the cannula distal end 98 has been inserted into the spine, the stylet 104 is removed. The injection into the spine is then made through the cannula. As in the previously described embodiments of the invention, the embodiment of the needle shown in FIG. 7A may be used in administering spinal injections while avoiding post dural puncture headache.

From the above descriptions of the various embodiments of the spinal injection needle of the invention, it is clear that various different types of needles currently employed in administering spinal injections can be improved by having the needles formed with a slight bend or curvature as in the needles of the present invention. This results in the needle distal end penetrating the spine tangentially and thereby avoiding post dural puncture headaches in the manner explained previously.

While the present invention has been described by reference to specific embodiments, it should be understood that modifications and variations of the invention may be constructed without departing from the scope of the invention defined in the following claims.

What is claimed:

1. In a spinal injection needle of the type employed in administering spinal anesthetics, the needle being comprised of a cannula having a longitudinal length with opposite proximal and distal ends and an opening at its distal end, the improvement comprising:

the needle cannula having a continuous curvature along at least one quarter of its longitudinal length;

the opening is positioned on one side of the cannula and the curvature of the cannula gives the cannula opposite concave and convex sides, the opening faces toward the convex side of the cannula and away from the concave side; and, the cannula has a beveled edge surrounding the opening at the cannula distal end, the beveled edge of the cannula is positioned in a plane, and a stylet having the same curvature of the cannula is inserted through the cannula from the cannula proximal end, the stylet has a distal end surface positioned in the same plane as the needle opening beveled edge.

2. In a spinal injection needle comprising a cannula having opposite proximal and distal ends;

means on the proximal end of the canula for attaching the cannula to a means for dispensing a medicament through the cannula to its distal end;

an opening at the cannula distal end for dispensing medicament from the cannula, the improvement comprising:

a continuous bend formed in at least one quarter of the length of the cannula wherein;

the cannula has opposite concave and convex exterior surfaces, and the opening in the cannula distal end faces in a direction away from the cannula convex surface and toward the concave surface;

the cannula has a beveled edge surrounding the opening at the cannula distal end, the beveled edge of the cannula is positioned in a plane, and a stylet having the same curvature of the cannula is inserted through the cannula from the cannula proximal end, the stylet has a distal end surface positioned in the same plane as the needle opening beveled edge.

3. In a spinal injection needle of the type employed in administering spinal anesthetics, the needle being comprised of a cannula having a longitudinal length with opposite proximal and distal ends and an opening at its distal end, the improvement comprising:

the needle cannula having a continuous curvature along at least one quarter of its longitudinal length; and, a stylet having the same curvature as the cannula inserted through the cannula from the cannula proximal end, the stylet has a longitudinal length greater than the length of the cannula, and the stylet has a distal end with a pointed tip that projects from the opening at the cannula distal end.

4. The improved spinal needle of claim 3, wherein:

the needle cannula curvature extends along one third of its longitudinal length adjacent its distal end.

5. In a spinal injection needle comprising a cannula having opposite proximal and distal ends;

means on the proximal end of the cannula for attaching the cannula to a means for dispensing a medicament through the cannula to its distal end;

an opening at the cannula distal end for dispensing medicament from the cannula, the improvement comprising:

a continuous bend formed in at least one quarter of the length of the cannula; and a stylet having the same curvature as the cannula inserted through the cannula from the cannula proximal end, the stylet has a longitudinal length greater than the length of the cannula, and the stylet has a distal end with a pointed tip that projects from the opening at the cannula distal end.

6. The needle of claim 5, wherein:

the continuous bend extends along at least one third of the cannula adjacent its distal end.

* * * * *